(12) United States Patent  
Ziemek et al.

(10) Patent No.: US 8,998,961 B1  
(45) Date of Patent: Apr. 7, 2015

(54) SPINAL ROD CONNECTOR AND METHODS

(75) Inventors: Terrence Ziemek, Broomfield, CO (US); Gregory Causey, Broomfield, CO (US)

(73) Assignee: Lanx, Inc., Broomfield, CO (US)

( * ) Notice: Subject to any disclaimer, the term of this patent is extended or adjusted under 35 U.S.C. 154(b) by 1077 days.

(21) Appl. No.: 12/393,980

(22) Filed: Feb. 26, 2009

(51) Int. Cl.
*A61B 17/70* (2006.01)
*A61B 17/86* (2006.01)

(52) U.S. Cl.
CPC ....................... *A61B 17/86* (2013.01)

(58) Field of Classification Search
USPC ......... 606/60, 53, 54, 59, 246, 250–253, 256, 606/258, 259, 260–262, 277, 278, 324; 403/59, 73, 103, 104, 169–179, 389, 403/391, 396
See application file for complete search history.

(56) References Cited

U.S. PATENT DOCUMENTS

| | | | |
|---|---|---|---|
| 2,249,658 A * | 7/1941 | Kemner | 403/173 |
| 2,970,798 A * | 2/1961 | Friotchle et al. | 248/229.25 |
| 4,294,561 A * | 10/1981 | Chapman et al. | 403/219 |
| 4,326,354 A * | 4/1982 | Hagberg | 446/126 |
| 4,569,338 A | 2/1986 | Edwards | |
| 4,573,459 A * | 3/1986 | Litton | 606/58 |
| 4,628,921 A * | 12/1986 | Rousso | 606/54 |
| 4,887,596 A | 12/1989 | Sherman | |
| 4,946,458 A | 8/1990 | Harms et al. | |
| 5,000,165 A | 3/1991 | Watanabe | |
| 5,067,955 A | 11/1991 | Cotrel | |
| 5,084,049 A | 1/1992 | Asher et al. | |
| 5,120,171 A | 6/1992 | Lasner | |
| 5,133,717 A * | 7/1992 | Chopin | 606/301 |
| 5,147,360 A | 9/1992 | Dubousset | |
| 5,190,543 A | 3/1993 | Schläpfer | |
| 5,207,678 A | 5/1993 | Harms et al. | |
| 5,226,766 A | 7/1993 | Lasner | |
| 5,275,600 A | 1/1994 | Allard et al. | |
| 5,312,404 A | 5/1994 | Asher et al. | |
| 5,312,405 A | 5/1994 | Korotko et al. | |
| 5,374,267 A | 12/1994 | Siegal | |
| 5,380,325 A | 1/1995 | Lahille et al. | |
| 5,382,248 A | 1/1995 | Jacobson et al. | |
| 5,387,212 A | 2/1995 | Yuan et al. | |
| 5,395,371 A | 3/1995 | Miller et al. | |
| 5,417,533 A | 5/1995 | Lasner | |

(Continued)

FOREIGN PATENT DOCUMENTS

EP 1 354 563 A2 10/2003
FR 2693365 1/1994

(Continued)

OTHER PUBLICATIONS

Notification of Transmittal of the International Search Report and the Written Opinion of the International Searching Authority, or the Declaration for PCT/US08/50912 Mailed Jul. 30, 2008.

(Continued)

*Primary Examiner* — Pedro Philogene
*Assistant Examiner* — Lynnsy Summitt
(74) *Attorney, Agent, or Firm* — Harness, Dickey

(57) ABSTRACT

A spine rod connector includes a base member and a plurality of set screws. The base member includes multiple apertures or bores arranged in different relative orientations. The spine rod connector is configured to couple at least two non aligned rods to each other.

22 Claims, 13 Drawing Sheets

(56) References Cited

U.S. PATENT DOCUMENTS

| | | |
|---|---|---|
| 5,429,639 A | 7/1995 | Judet |
| 5,437,669 A | 8/1995 | Yuan et al. |
| 5,437,671 A | 8/1995 | Lozier et al. |
| 5,466,237 A | 11/1995 | Byrd, III et al. |
| 5,468,241 A | 11/1995 | Metz-Stavenhagen et al. |
| 5,474,555 A | 12/1995 | Puno et al. |
| 5,486,174 A | 1/1996 | Fournet-Fayard et al. |
| 5,487,742 A | 1/1996 | Cotrel |
| 5,492,442 A | 2/1996 | Lasner |
| 5,499,983 A | 3/1996 | Hughes |
| 5,505,731 A | 4/1996 | Tornier |
| 5,507,745 A | 4/1996 | Logroscino et al. |
| 5,514,132 A | 5/1996 | Csernatony et al. |
| 5,520,689 A | 5/1996 | Schläpfer et al. |
| 5,522,816 A | 6/1996 | Dinello et al. |
| 5,527,314 A * | 6/1996 | Brumfield et al. ............ 606/278 |
| 5,531,746 A | 7/1996 | Errico et al. |
| 5,534,002 A * | 7/1996 | Brumfield et al. ............ 606/278 |
| 5,536,268 A | 7/1996 | Griss |
| 5,540,690 A | 7/1996 | Miller et al. |
| 5,542,946 A | 8/1996 | Logroscino et al. |
| 5,549,608 A | 8/1996 | Errico et al. |
| 5,554,157 A | 9/1996 | Errico et al. |
| 5,562,662 A | 10/1996 | Brumfield et al. |
| 5,569,246 A | 10/1996 | Ojima et al. |
| 5,569,247 A | 10/1996 | Morrison |
| 5,569,248 A | 10/1996 | Mathews |
| 5,584,834 A | 12/1996 | Errico et al. |
| 5,586,984 A | 12/1996 | Errico et al. |
| 5,591,165 A | 1/1997 | Jackson |
| 5,591,166 A | 1/1997 | Bernhardt et al. |
| 5,601,552 A | 2/1997 | Cotrel |
| 5,607,425 A | 3/1997 | Rogozinski et al. |
| 5,607,426 A | 3/1997 | Ralph et al. |
| 5,609,592 A | 3/1997 | Brumfield et al. |
| 5,624,442 A | 4/1997 | Mellinger et al. |
| 5,628,740 A | 5/1997 | Mullane |
| 5,634,925 A | 6/1997 | Urbanski |
| 5,643,264 A | 7/1997 | Sherman et al. |
| 5,647,873 A | 7/1997 | Errico et al. |
| 5,651,789 A | 7/1997 | Cotrel |
| 5,653,708 A | 8/1997 | Howland |
| 5,662,653 A | 9/1997 | Songer et al. |
| 5,667,506 A | 9/1997 | Sutterlin |
| 5,669,910 A | 9/1997 | Korhonen et al. |
| 5,669,911 A | 9/1997 | Errico et al. |
| 5,672,176 A | 9/1997 | Biedermann et al. |
| 5,683,390 A | 11/1997 | Metz-Stavenhagen et al. |
| 5,688,272 A | 11/1997 | Montague et al. |
| 5,690,630 A | 11/1997 | Errico et al. |
| 5,693,053 A | 12/1997 | Estes |
| 5,702,395 A | 12/1997 | Hopf |
| 5,702,452 A * | 12/1997 | Argenson et al. ............ 606/253 |
| 5,716,355 A | 2/1998 | Jackson et al. |
| 5,725,528 A | 3/1998 | Errico et al. |
| 5,728,098 A | 3/1998 | Sherman et al. |
| 5,733,286 A | 3/1998 | Errico et al. |
| 5,735,851 A | 4/1998 | Errico et al. |
| 5,738,685 A | 4/1998 | Halm et al. |
| 5,743,911 A | 4/1998 | Cotrel |
| 5,752,955 A | 5/1998 | Errico |
| 5,752,957 A | 5/1998 | Ralph et al. |
| 5,776,135 A | 7/1998 | Errico et al. |
| 5,782,833 A | 7/1998 | Haider |
| 5,785,711 A | 7/1998 | Errico et al. |
| 5,800,548 A | 9/1998 | Martin et al. |
| 5,810,819 A | 9/1998 | Errico et al. |
| 5,814,046 A | 9/1998 | Hopf |
| 5,817,094 A | 10/1998 | Errico et al. |
| 5,863,293 A | 1/1999 | Richelsoph |
| 5,879,350 A | 3/1999 | Sherman et al. |
| 5,882,350 A | 3/1999 | Ralph et al. |
| 5,891,145 A | 4/1999 | Morrison et al. |
| 5,899,903 A | 5/1999 | Cotrel |
| 5,910,142 A | 6/1999 | Tatar |
| 5,947,966 A | 9/1999 | Drewry et al. |
| 5,954,725 A | 9/1999 | Sherman et al. |
| 5,961,518 A | 10/1999 | Errico et al. |
| 5,964,760 A | 10/1999 | Richelsoph |
| 5,980,521 A | 11/1999 | Montague et al. |
| 5,980,523 A | 11/1999 | Jackson |
| 5,984,922 A | 11/1999 | McKay |
| 5,989,250 A | 11/1999 | Wagner et al. |
| 5,989,251 A | 11/1999 | Nichols |
| 5,989,254 A | 11/1999 | Katz |
| 5,997,539 A | 12/1999 | Errico et al. |
| 6,004,332 A | 12/1999 | Yoon et al. |
| 6,015,409 A | 1/2000 | Jackson |
| 6,017,344 A | 1/2000 | Errico et al. |
| 6,053,917 A | 4/2000 | Sherman et al. |
| 6,063,089 A | 5/2000 | Errico et al. |
| 6,074,393 A | 6/2000 | Sitoto |
| 6,083,226 A | 7/2000 | Fiz |
| 6,090,111 A | 7/2000 | Nichols |
| 6,096,039 A | 8/2000 | Stoltenberg et al. |
| 6,110,173 A | 8/2000 | Thomas, Jr. |
| 6,113,600 A | 9/2000 | Drummond et al. |
| 6,113,601 A | 9/2000 | Tatar |
| 6,132,430 A | 10/2000 | Wagner |
| 6,132,434 A | 10/2000 | Sherman et al. |
| 6,136,003 A | 10/2000 | Hoeck et al. |
| 6,139,548 A | 10/2000 | Errico |
| 6,171,311 B1 | 1/2001 | Richelsoph |
| 6,179,838 B1 | 1/2001 | Fiz |
| 6,183,472 B1 | 2/2001 | Lutz |
| 6,217,578 B1 | 4/2001 | Crozet et al. |
| 6,224,598 B1 | 5/2001 | Jackson |
| 6,234,705 B1 | 5/2001 | Troxell |
| 6,238,396 B1 | 5/2001 | Lombardo |
| 6,241,731 B1 | 6/2001 | Fiz |
| 6,283,967 B1 | 9/2001 | Troxell et al. |
| 6,287,311 B1 | 9/2001 | Sherman et al. |
| 6,299,614 B1 | 10/2001 | Kretschmer et al. |
| 6,302,882 B1 | 10/2001 | Lin et al. |
| 6,306,137 B2 | 10/2001 | Troxell |
| 6,325,802 B1 | 12/2001 | Frigg |
| 6,328,740 B1 | 12/2001 | Richelsoph |
| 6,328,741 B1 | 12/2001 | Richelsoph |
| 6,361,535 B2 | 3/2002 | Jackson |
| RE37,665 E | 4/2002 | Ralph et al. |
| 6,368,320 B1 | 4/2002 | Le Couedic et al. |
| 6,368,321 B1 | 4/2002 | Jackson |
| 6,379,354 B1 | 4/2002 | Rogozinski |
| 6,402,751 B1 | 6/2002 | Hoeck et al. |
| 6,402,752 B2 | 6/2002 | Schäffler-Wachter et al. |
| 6,413,257 B1 | 7/2002 | Lin et al. |
| 6,413,258 B1 | 7/2002 | Bernhardt, Jr. |
| 6,416,515 B1 | 7/2002 | Wagner |
| 6,423,064 B1 | 7/2002 | Kluger |
| 6,432,108 B1 | 8/2002 | Burgess et al. |
| 6,440,132 B1 | 8/2002 | Jackson |
| 6,440,137 B1 | 8/2002 | Horwarth et al. |
| 6,451,021 B1 | 9/2002 | Ralph et al. |
| 6,454,773 B1 | 9/2002 | Sherman et al. |
| 6,468,276 B1 | 10/2002 | McKay |
| 6,478,798 B1 | 11/2002 | Howland |
| 6,482,207 B1 | 11/2002 | Errico |
| 6,485,494 B1 | 11/2002 | Haider |
| 6,488,681 B2 | 12/2002 | Martin et al. |
| 6,520,444 B1 | 2/2003 | Muller |
| 6,524,310 B1 | 2/2003 | Lombardo et al. |
| 6,533,790 B1 | 3/2003 | Liu |
| 6,540,748 B2 | 4/2003 | Lombardo |
| 6,540,749 B2 | 4/2003 | Schäfer et al. |
| 6,547,789 B1 | 4/2003 | Ventre et al. |
| 6,554,832 B2 | 4/2003 | Shluzas |
| 6,554,834 B1 | 4/2003 | Crozet et al. |
| 6,562,040 B1 | 5/2003 | Wagner |
| 6,565,566 B1 | 5/2003 | Wagner et al. |
| 6,565,567 B1 | 5/2003 | Haider |
| 6,585,740 B2 | 7/2003 | Schlapfer et al. |
| 6,589,243 B1 | 7/2003 | Viart et al. |
| 6,595,992 B1 | 7/2003 | Wagner et al. |
| 6,602,253 B2 | 8/2003 | Richelsoph et al. |

(56) References Cited

U.S. PATENT DOCUMENTS

| | | |
|---|---|---|
| 6,610,062 B2 | 8/2003 | Balley et al. |
| 6,613,050 B1 | 9/2003 | Wagner et al. |
| 6,616,668 B2 | 9/2003 | Altarac et al. |
| 6,626,908 B2 | 9/2003 | Cooper et al. |
| 6,626,909 B2 | 9/2003 | Chin |
| 6,645,207 B2 | 11/2003 | Dixon et al. |
| 6,673,073 B1 | 1/2004 | Schafer |
| 6,685,705 B1 * | 2/2004 | Taylor ............................ 606/278 |
| 6,716,213 B2 | 4/2004 | Shitoto |
| 6,736,817 B2 | 5/2004 | Troxell et al. |
| 6,752,807 B2 | 6/2004 | Lin et al. |
| 6,761,721 B2 | 7/2004 | Burgess et al. |
| 6,783,526 B1 | 8/2004 | Lin et al. |
| 6,786,907 B2 | 9/2004 | Lange |
| 6,802,844 B2 | 10/2004 | Ferree |
| 6,872,208 B1 | 3/2005 | McBride et al. |
| 6,875,211 B2 | 4/2005 | Nichols et al. |
| 6,887,241 B1 | 5/2005 | McBride et al. |
| 6,896,677 B1 | 5/2005 | Lin |
| 6,974,460 B2 | 12/2005 | Carbone et al. |
| 7,063,481 B2 * | 6/2006 | Trull ............................. 403/170 |
| 7,122,036 B2 | 10/2006 | Vanacker |
| 7,137,986 B2 | 11/2006 | Troxell et al. |
| 7,160,301 B2 | 1/2007 | Cordaro |
| 7,163,539 B2 | 1/2007 | Abdelgany et al. |
| 7,166,108 B2 | 1/2007 | Mazda et al. |
| 7,166,109 B2 | 1/2007 | Biedermann et al. |
| 7,175,622 B2 * | 2/2007 | Farris ............................ 606/250 |
| 7,186,255 B2 | 3/2007 | Baynham et al. |
| 7,211,086 B2 | 5/2007 | Biedermann et al. |
| 7,794,478 B2 * | 9/2010 | Nilsson ........................ 606/251 |
| 2001/0047171 A1 | 11/2001 | Troxell et al. |
| 2002/0007183 A1 | 1/2002 | Lee et al. |
| 2002/0010467 A1 | 1/2002 | Cooper et al. |
| 2002/0032442 A1 | 3/2002 | Altarac et al. |
| 2002/0040223 A1 | 4/2002 | Sato et al. |
| 2002/0052603 A1 | 5/2002 | Nichols et al. |
| 2002/0068937 A1 * | 6/2002 | Kuntz ............................. 606/60 |
| 2002/0111625 A1 | 8/2002 | Richelsoph et al. |
| 2002/0138077 A1 | 9/2002 | Farree |
| 2002/0143330 A1 | 10/2002 | Shluzas |
| 2002/0169448 A1 | 11/2002 | Vanacker |
| 2002/0169450 A1 | 11/2002 | Lange |
| 2002/0183749 A1 | 12/2002 | Burgess et al. |
| 2003/0018334 A1 | 1/2003 | Richelsoph et al. |
| 2003/0032959 A1 * | 2/2003 | Yeh ............................... 606/61 |
| 2003/0045874 A1 | 3/2003 | Thomas, Jr. |
| 2003/0078580 A1 | 4/2003 | Shitoto |
| 2003/0083659 A1 | 5/2003 | Lin et al. |
| 2003/0114853 A1 | 6/2003 | Burgess et al. |
| 2003/0125742 A1 | 7/2003 | Yuan et al. |
| 2003/0163132 A1 | 8/2003 | Chin |
| 2003/0171751 A1 | 9/2003 | Ritland |
| 2004/0015166 A1 | 1/2004 | Gorek |
| 2004/0049188 A1 | 3/2004 | Slivka et al. |
| 2004/0116928 A1 | 6/2004 | Young et al. |
| 2004/0122425 A1 | 6/2004 | Suzuki et al. |
| 2004/0133202 A1 | 7/2004 | Suzuki et al. |
| 2004/0133203 A1 | 7/2004 | Young et al. |
| 2004/0143265 A1 | 7/2004 | Landry et al. |
| 2004/0153077 A1 | 8/2004 | Biedermann et al. |
| 2004/0172024 A1 | 9/2004 | Gorek |
| 2004/0176766 A1 | 9/2004 | Shluzas |
| 2004/0181223 A1 | 9/2004 | Ritland |
| 2004/0236330 A1 | 11/2004 | Purcell et al. |
| 2004/0260287 A1 | 12/2004 | Ferree |
| 2005/0010222 A1 | 1/2005 | Cordaro |
| 2005/0033295 A1 | 2/2005 | Wisnewski |
| 2005/0080415 A1 | 4/2005 | Keyer et al. |
| 2005/0080420 A1 * | 4/2005 | Farris et al. ....................... 606/61 |
| 2005/0090821 A1 | 4/2005 | Berrevoets et al. |
| 2005/0107789 A1 | 5/2005 | Sweeney |
| 2005/0113830 A1 | 5/2005 | Rezach et al. |
| 2005/0137594 A1 | 6/2005 | Doubler et al. |
| 2005/0143823 A1 | 6/2005 | Boyd et al. |
| 2005/0149019 A1 | 7/2005 | Sasing et al. |
| 2005/0149023 A1 | 7/2005 | Ritland |
| 2005/0154390 A1 | 7/2005 | Biedermann et al. |
| 2005/0177154 A1 | 8/2005 | Moumene et al. |
| 2005/0187548 A1 | 8/2005 | Butler et al. |
| 2005/0192571 A1 | 9/2005 | Abdelgany |
| 2005/0203515 A1 | 9/2005 | Doherty et al. |
| 2005/0228377 A1 | 10/2005 | Chao et al. |
| 2005/0277928 A1 | 12/2005 | Boschert |
| 2006/0036240 A1 | 2/2006 | Colleran et al. |
| 2006/0079892 A1 * | 4/2006 | Roychowdhury et al. ...... 606/61 |
| 2006/0142761 A1 | 6/2006 | Landry et al. |
| 2006/0206114 A1 | 9/2006 | Ensign et al. |
| 2006/0229607 A1 | 10/2006 | Brumfield |
| 2006/0233597 A1 * | 10/2006 | Ensign et al. .................. 403/177 |
| 2006/0241598 A1 | 10/2006 | Khalili |
| 2006/0241602 A1 | 10/2006 | Jackson |
| 2006/0241769 A1 | 10/2006 | Gordon et al. |
| 2006/0247626 A1 | 11/2006 | Taylor et al. |
| 2006/0247629 A1 * | 11/2006 | Maughan et al. ............... 606/61 |
| 2006/0271045 A1 | 11/2006 | Hubbard et al. |
| 2006/0271046 A1 | 11/2006 | Kwak et al. |
| 2006/0271051 A1 | 11/2006 | Berrevoets et al. |
| 2007/0016197 A1 | 1/2007 | Woods et al. |
| 2007/0049932 A1 | 3/2007 | Richelsoph et al. |
| 2007/0179501 A1 * | 8/2007 | Firkins ............................ 606/61 |
| 2008/0215095 A1 * | 9/2008 | Biedermann et al. ......... 606/246 |
| 2008/0243186 A1 * | 10/2008 | Abdou ........................... 606/246 |
| 2008/0262553 A1 * | 10/2008 | Hawkins et al. .............. 606/278 |
| 2010/0280552 A1 * | 11/2010 | Lee ................................ 606/250 |
| 2011/0004248 A1 * | 1/2011 | Abdou ........................... 606/250 |
| 2011/0245872 A1 * | 10/2011 | Nilsson ......................... 606/250 |

FOREIGN PATENT DOCUMENTS

| | | |
|---|---|---|
| FR | 2734471 | 11/1996 |
| FR | 2740674 | 5/1997 |
| FR | 2789293 | 8/2000 |
| WO | WO 00/76413 | 12/2000 |
| WO | WO 01/97701 | 12/2001 |

OTHER PUBLICATIONS

Supplementary European Search Report, Feb. 23, 2009.

Notification Concerning Transmittal of International Preliminary Report on Patentability (Chapter I of the Patent Cooperation Treaty) for PCT/US05/27598 mailed Feb. 22, 2007.

Notification of Transmittal of the International Search Report and the Written Opinion of the International Searching Authority for PCT/US05/27596 mailed Oct. 10, 2006.

Notification Concerning Transmittal of International Preliminary Report on Patentability (Chapter I of the Patent Cooperation Treaty) for PCT/US08/50912 mailed Jul. 23, 2009.

Notification of Transmittal of the International Search Report and Written Opinion of the International Searching Authority, or the Declaration for PCT/US05/31253 mailed Mar. 14, 2006.

Acta Orthop Scand article dated Jun. 1984 by Bostman O. Myllynen P. Riska EB.

* cited by examiner

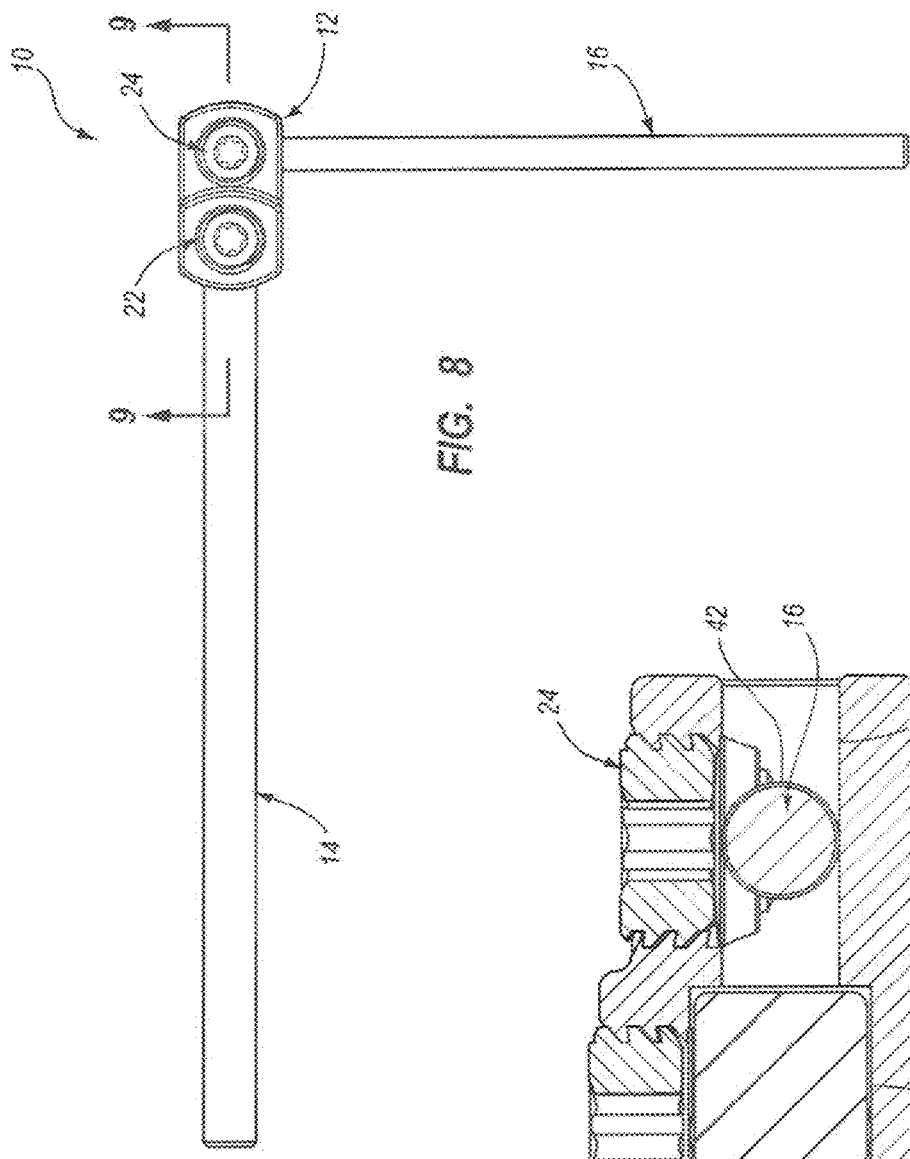

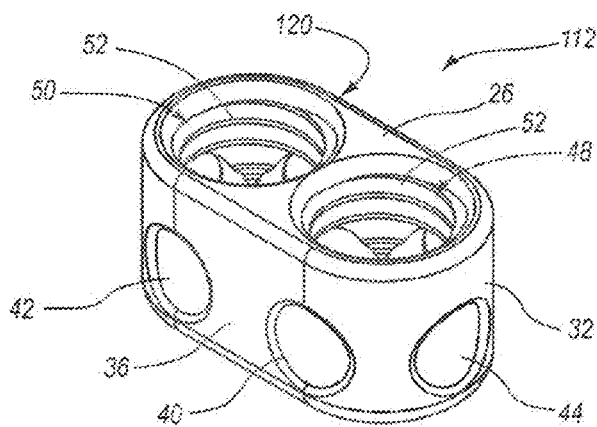
*FIG. 15*
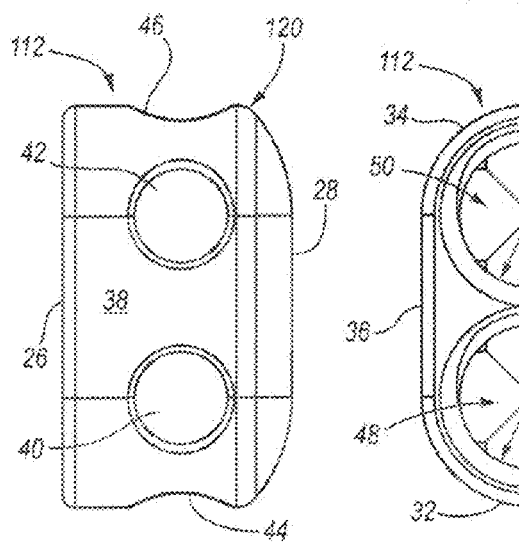 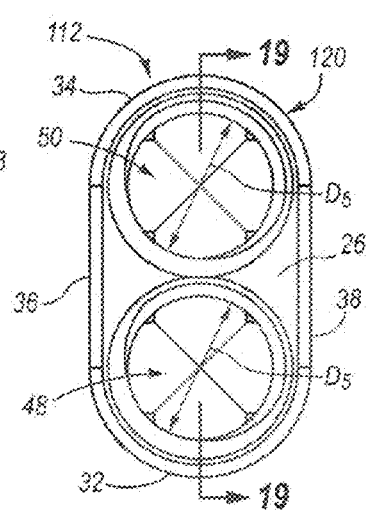 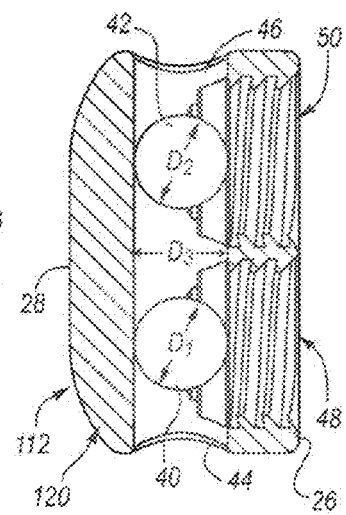
*FIG. 17*   *FIG. 16*   *FIG. 19*
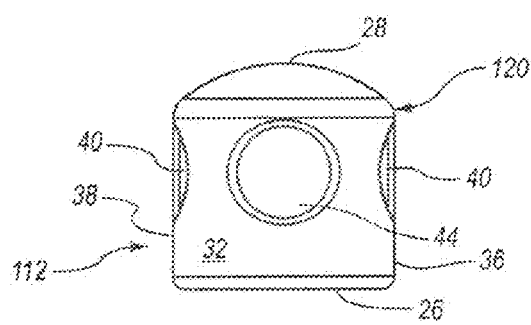
*FIG. 18*

US 8,998,961 B1

SPINAL ROD CONNECTOR AND METHODS

FIELD OF THE INVENTION

The present disclosure relates to a device for spinal fixation, and in particular to a connector for coupling multiple spinal rods together.

BACKGROUND

Various systems are available for use in spinal correction and fixation. These systems usually include a pair of elongate members, typically rods, placed along the vertebral column. Each rod is attached to the spine with various attachment devices. These attachment devices may include, for example, pedicle screws, pedicle hooks, plates, and similar devices.

Due to a wide variety of factors, the two rods are often not aligned in clinical situations. There are several ways to address the variations of alignment. In one example, one or both of the rods may be bent to accommodate the connector. However, any bending in either of the rods may adversely affect the fixation to the spine and comprise clinical outcome. Furthermore, the bending may also adversely affect the mechanical properties of the rods.

Connectors with some adjustability have been designed to adapt for variations in alignment. However, most are multi-piece systems that may be difficult to assemble and use in the surgical environment. Others are one-piece designs that do not allow for adjustments to compensate for various rod arrangements. Thus, there exists a need for an improved connector for coupling spinal rods.

SUMMARY

One aspect of the present disclosure relates to a spine rod connector that includes a base member and a plurality of set screws. The base member includes multiple apertures or bores arranged in different relative orientations for receipt of spine rods. The spine rod connector is configured to couple at least two non aligned rods to each other.

The foregoing and other features, utilities and advantages of the invention will be apparent from the following more particular description of a preferred embodiment of the invention as illustrated in the accompanying drawings.

BRIEF DESCRIPTION OF THE DRAWINGS

The accompanying drawings, which are incorporated in and constitute a part of this specification, illustrate embodiments of the present invention, and together with the description, serve to explain the principles thereof. Like items in the drawings are referred to using the same numerical reference.

FIG. 8 is a top view of the spine rod connector assembly of FIG. 7;

FIG. 9 is a cross-sectional view of the spine rod connector assembly of FIG. 8;

FIG. 15 is a perspective view of another spine rod connector according to the present disclosure;

FIG. 16 is a top view of the spine rod connector of FIG. 15;

FIG. 17 is a side view of the spine rod connector of FIG. 15;

FIG. 18 is an end view of the spine rod connector of FIG. 15;

FIG. 19 is a cross-sectional view of the spine rod connector of FIG. 16;

DETAILED DESCRIPTION

The present disclosure is directed to a spine rod connector assembly that includes a spine rod connector configured to couple together a plurality of spinal rods used for treatment of a person's spine. The spine rod connector is configured with a plurality of apertures or bores that are sized to receive the spine rods in various orientations relative to each other. The spine rod connector may include at least one connecting device (e.g., a set screw or other fastener) that secures the spine rods to the spine rod connector. In some arrangements, the connecting device provides releasable coupling of the spine rods to the spine rod connector. In other arrangements, the connecting device provides a permanent connection between the spine rods and the spine rod connector.

In one example, as will be described in further detail below, the spine rod connector includes at least two bores that are arranged and configured to allow non aligned spine rods to be coupled to the connector and at least one other bore that is arranged angled to the other bores. Inserting portions of the spine rods into the bores of the spine rod connector may result in a variety of relative orientations for the spine rods including, for example, in parallel, radially spaced apart orientations (i.e., side-by-side), in axially aligned orientations (i.e., end-to-end), angled orientations, or perpendicular orientations.

The spine rod connector may include different sized and shaped bores to receive various sized spine rods having a variety of cross-sectional shapes. In at least one example, the spine rod connector includes a first pair of bores arranged perpendicular to each other. The bores of the first pair of bores may each have a first diameter. The bores of a second pair of bores may be arranged perpendicular to each other. The bores of the second pair of bore may each have a second diameter that is smaller than the first diameter. A set screw or other connecting device may be associated with each pair of bores. The set screws are operable to secure a spine rod in each of the pairs of bores. In some arrangements, the spine rod connector includes three or more pairs of bores. A set screw or other connecting devices may be associated with each pair of bores and operable to couple a spine rod in each of the pairs of bores.

Figure 1:
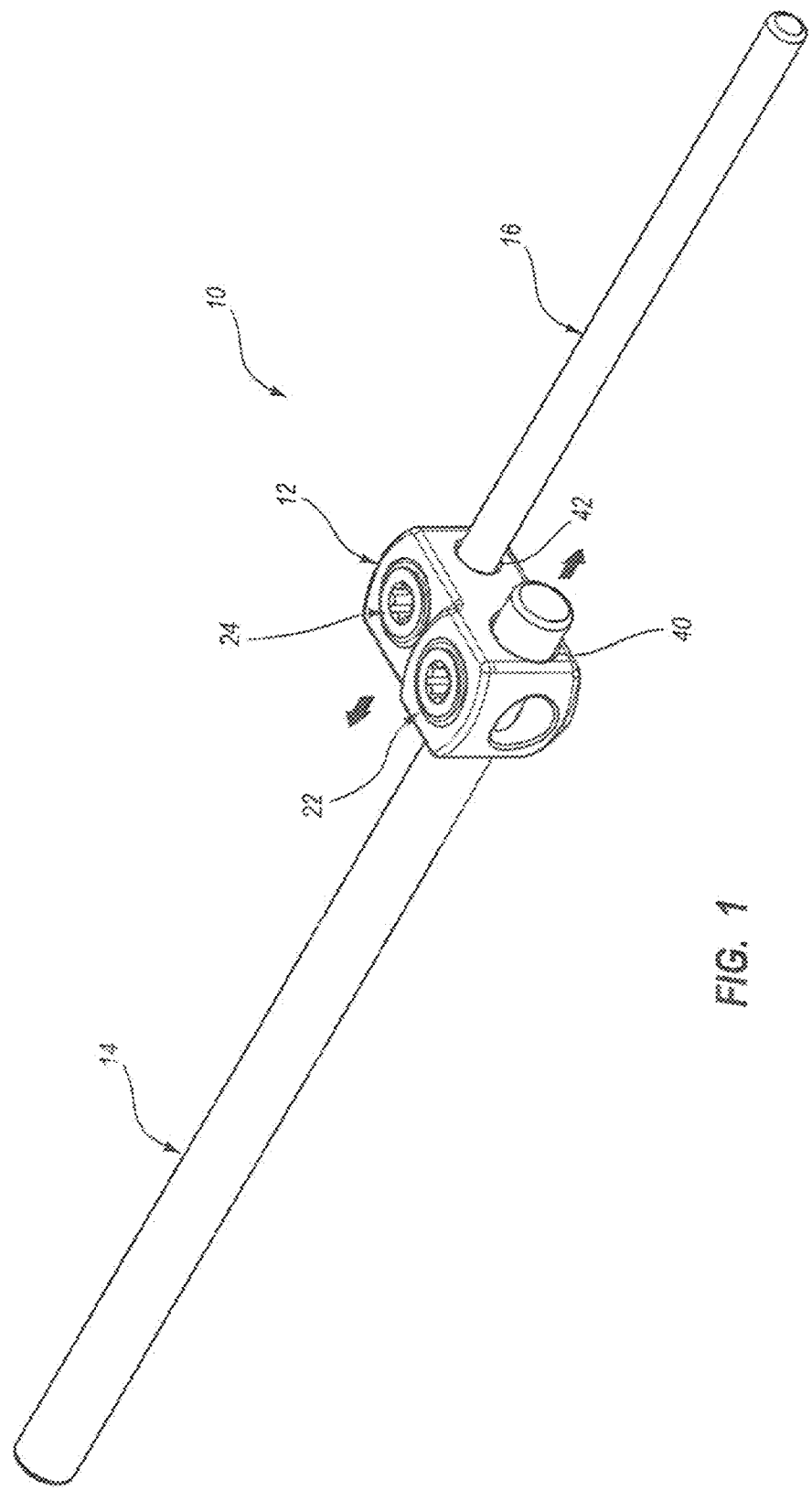
FIG. 1 is a perspective view of a spine rod connector assembly according to the present disclosure in which the rods are in a first configuration.
Figure 2:
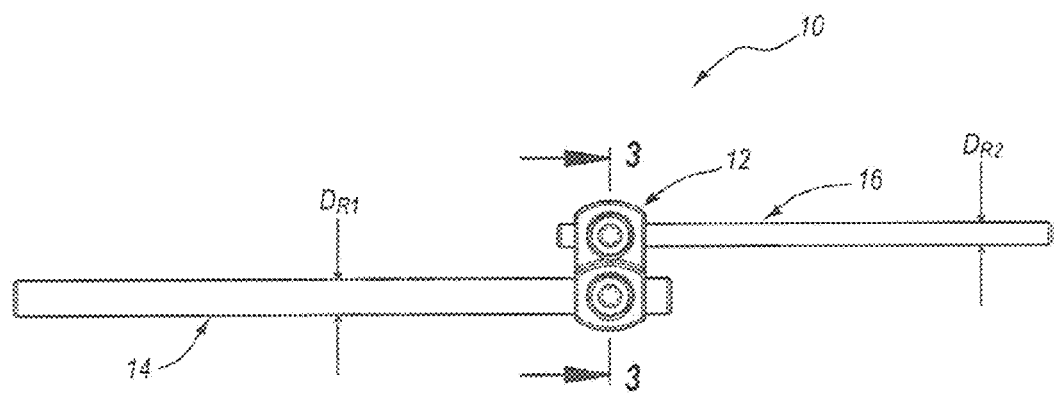
FIG. 2 is a top view of the spine rod connector assembly of FIG. 1.
Figure 3:
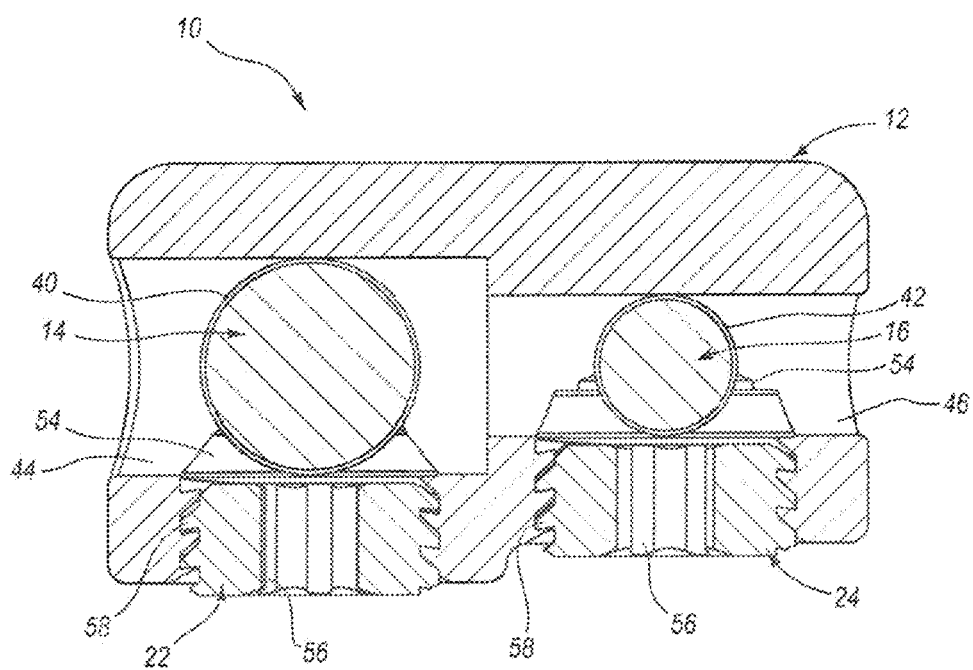
FIG. 3 is a cross-sectional view of the spine rod connector assembly of FIG. 2.
Figure 4:
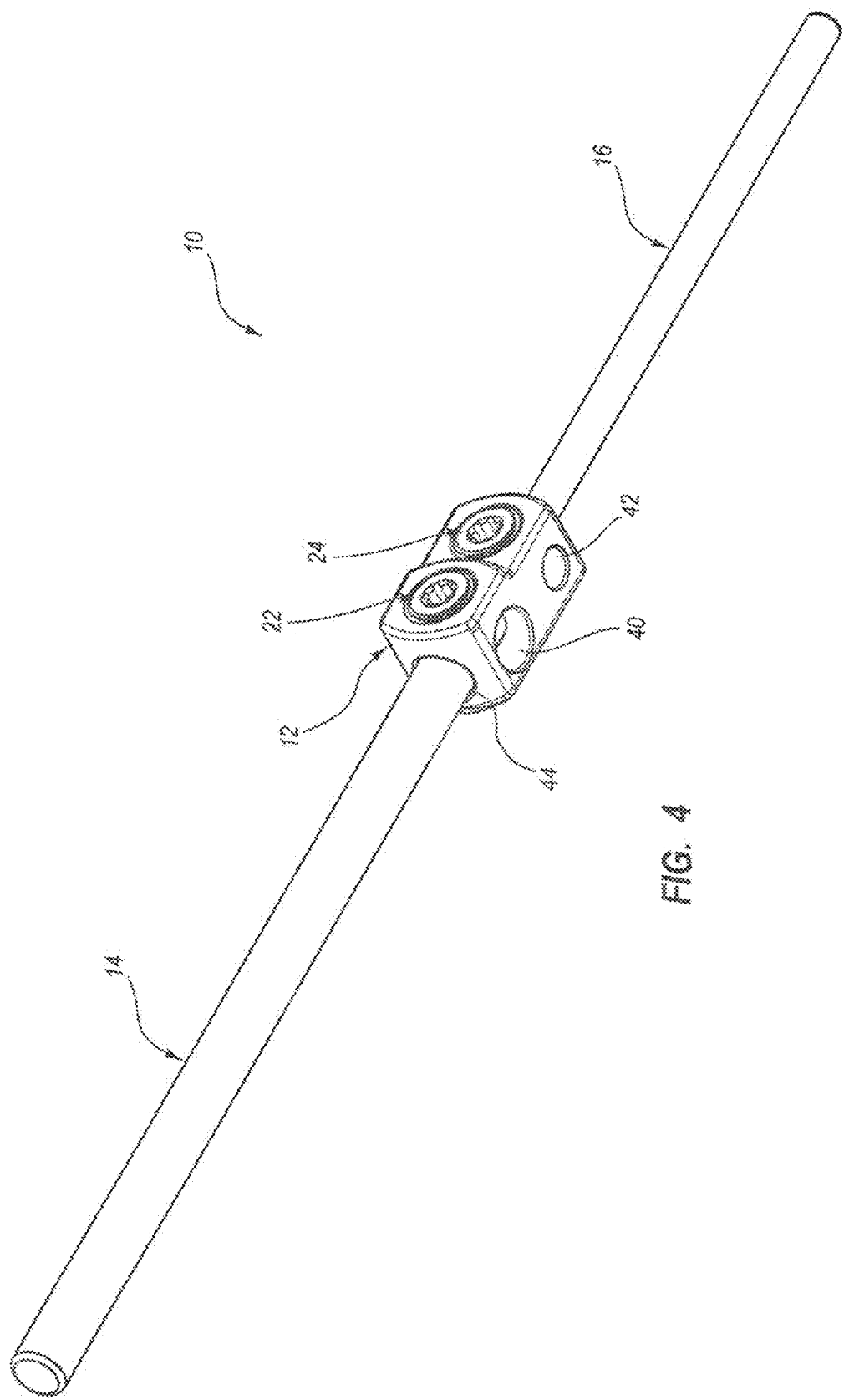
FIG. 4 is a perspective view of a spine rod connector assembly of FIG. 1 in which the rods are in a second configuration.
Figure 5:
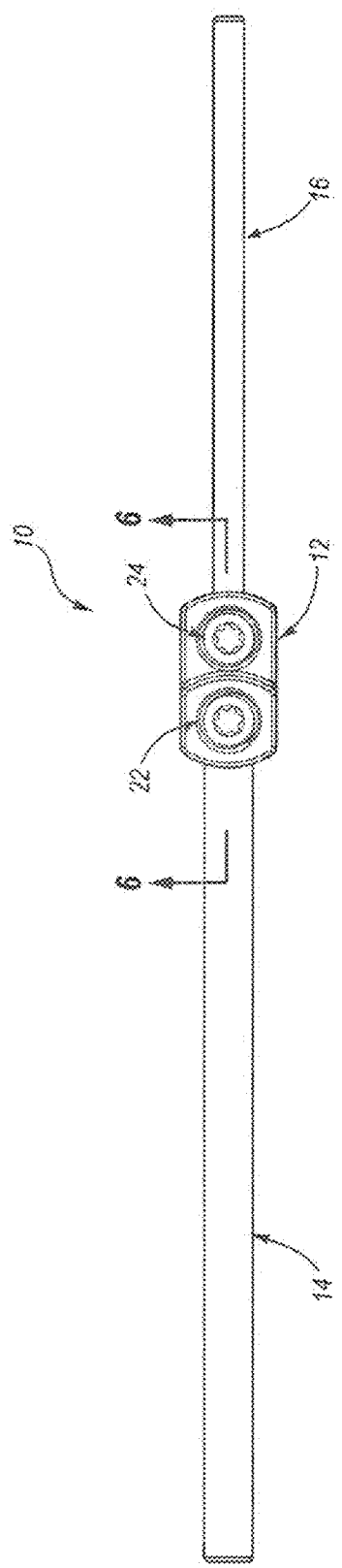
FIG. 5 is a top view of the spine rod connector assembly of FIG. 4.
Figure 6:
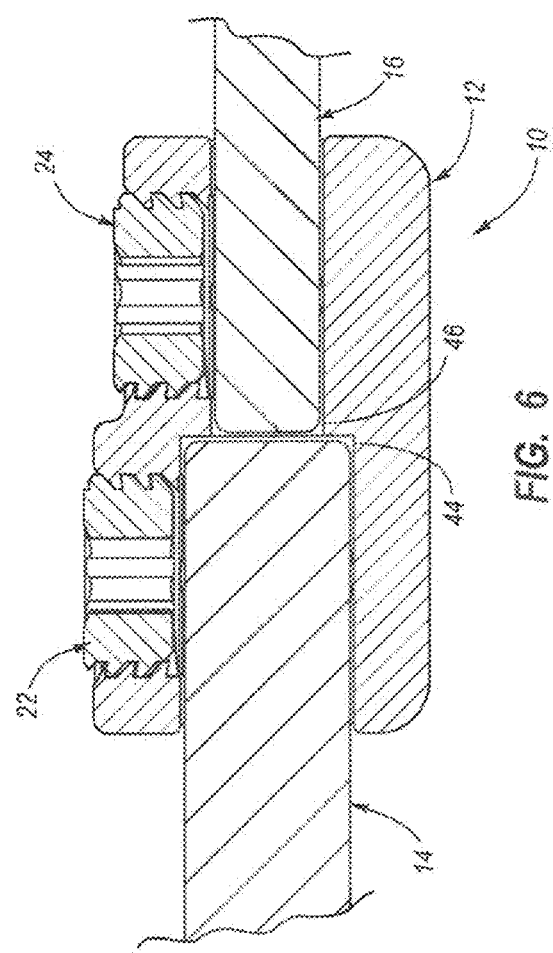
FIG. 6 is a cross-sectional view of the spines rod connector assembly of FIG. 5.
Figure 7:
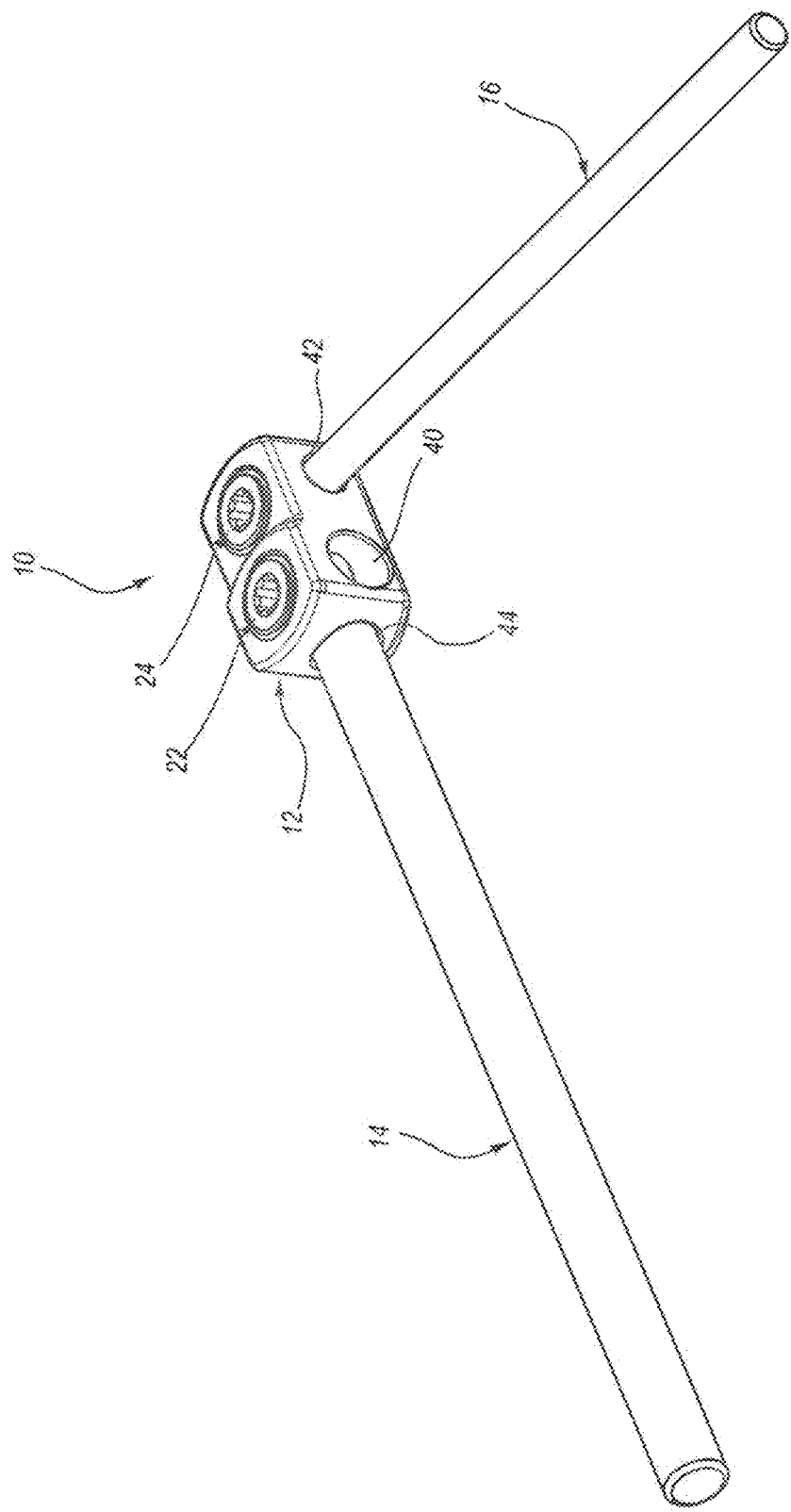
FIG. 7 is a perspective view of a spine rod connector assembly of FIG. 1 in which the rods are in a third configuration.

Referring now to FIGS. 1-14, an example spine rod connector assembly 10 is shown and described. The spine rod connector assembly 10 includes a spine rod connector 12 and first and second spine rods 14, 16. Three different arrangements of the first and second spine rods 14, 16 relative to each other and the spine rod connector 12 are illustrated in FIGS. 1-9. In FIGS. 1-3, the first and second spine rods 14, 16 are arranged parallel with each other and radially spaced apart from each other (also referred to as laterally spaced apart or side-by-side). In FIGS. 4-6, the spine rods 14, 16 are arranged in coaxial arrangement relative to each other. In FIGS. 7-9, the first and second spine rods 14, 16 are arranged perpendicular to each other.

The spine rod connector 12 includes a base portion 20, and first and second set screws 22, 24 (see FIGS. 1-3 and 10-14). The base portion 20 includes top and bottom surfaces 26, 28, front and rear surfaces 32, 34, and first and second side surfaces 36, 38. Typically, each of the pairs of surfaces 26, 28; 32, 34; 36, 38 are arranged generally perpendicular to each other. Any of the surfaces 26, 28, 32, 34, 36, 38 may be, for example, generally planer such as the general planer structure of surface 38 shown in FIG. 10, curved or contour shaped such as the surface 34 shown in FIG. 10, or stepped (e.g., having a step feature 30) such as the top surface 26 shown in FIG. 10. The step feature 30 defines a relatively sharp change in thickness of the base portion 20 between an area surrounding the aperture 48 to the area surrounding the aperture 50 along the surface 26. Alternatively, the step feature 30 can be a gradual offset such as a ramp or curved surface extending from an area surrounding the aperture 48 to the area surrounding the aperture 50 along the surface 26. Other configurations, shapes and sizes are possible for any one of the exterior surfaces of the base portion 20.

The descriptions of the connectors described herein generally refer to surfaces of the connector as having top, bottom, side, front, and/or rear surfaces. The connector in fact may be cylindrical and/or spherical in construction. In such cases, the surface refers to a bore orientation on the connector. For example, a spherical connector may have, for example, two bores in a front surface of the sphere.

The base portion 20 shown in FIGS. 1-14 has a generally cubic shape with rectangular cross-sections. Many other shapes are possible for the base portion including, for example, generally spherical shapes, or the shapes that include fewer or greater than the six surface structure shown in FIGS. 1-14.

The base portion 20 further includes first and second side rod apertures 40, 42, front and rear and apertures 44, 46, and first and second set screw apertures 48, 50. The first and second side rod apertures 40, 42 are shown having diameters D1, D2, respectively, that are different from each other. The front and rear end apertures 44, 46 have diameters D3, D4, respectively, that also are different from each other. The first and second set screw apertures 48, 50 have diameters D5, D6 that are substantially the same size. In other arrangements, any one of the diameters D1-D6 can be the same or different size. The first and second screw apertures 48, 50 include a plurality of internal threads 52 sized to mate with threads of the first and second set screws 22, 24.

Figure 10:
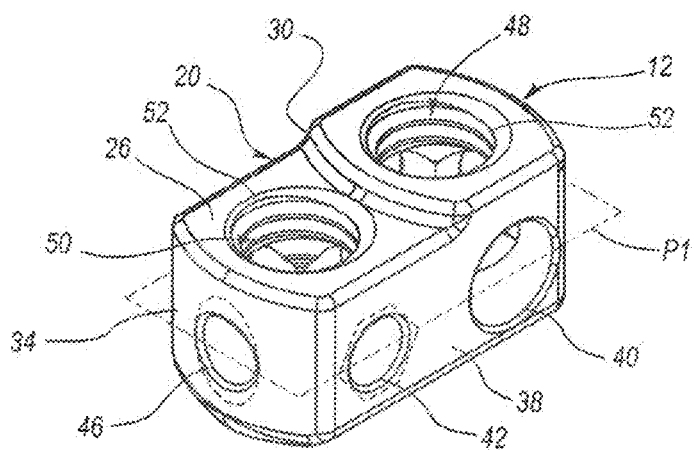
FIG. 10 is a perspective view of the spine rod connector of FIG. 1.
Figures 11, 12, 14:
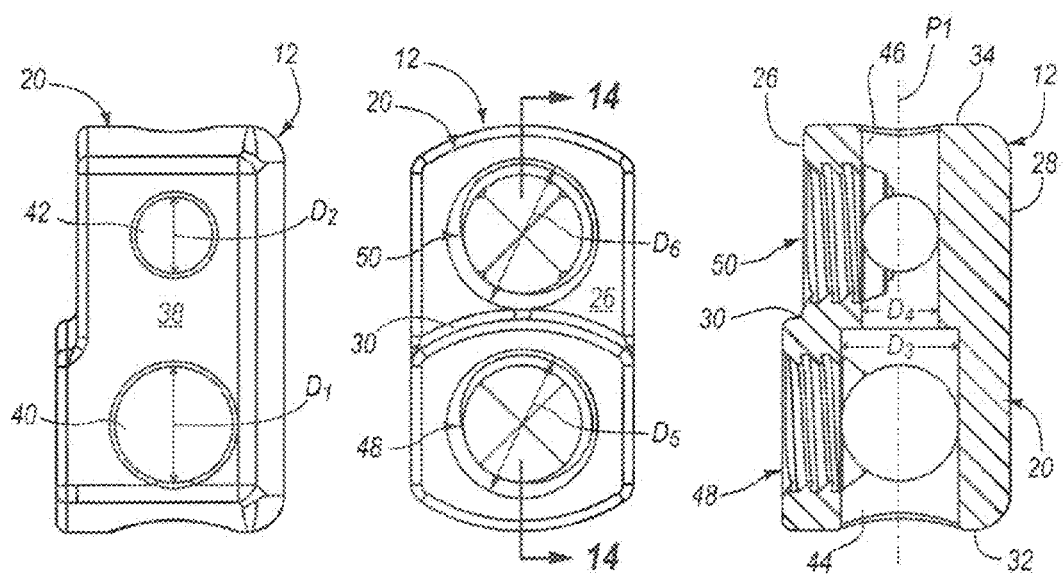
FIG. 11 is a top view of the spine rod connector of FIG. 1.
FIG. 12 is a side view of the spine rod connector of FIG. 1.
FIG. 14 is a cross-sectional view of the spine rod connector of FIG. 11.
Figure 13:
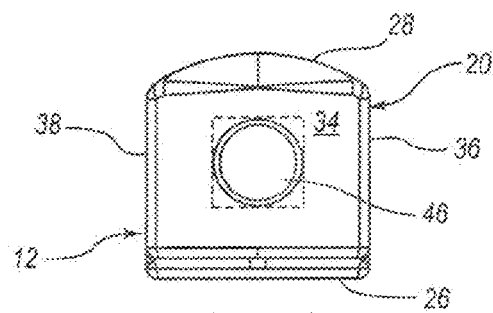
FIG. 13 is an end view of the spine rod connector of FIG. 1.
Figure 20:
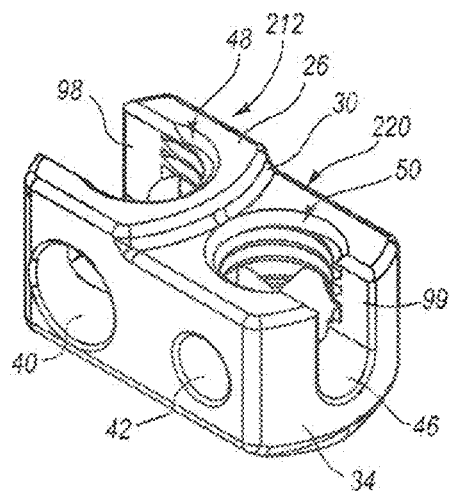
FIG. 20 is a perspective view of another spine rod connector according to the present disclosure.
Figure 21:
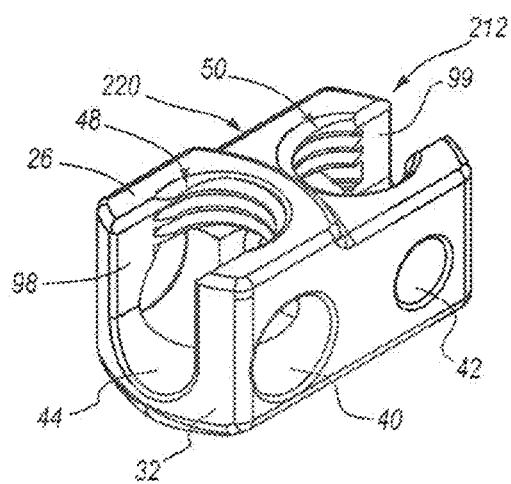
FIG. 21 is another perspective view of the spine rod connector of FIG. 20.
Figure 23:
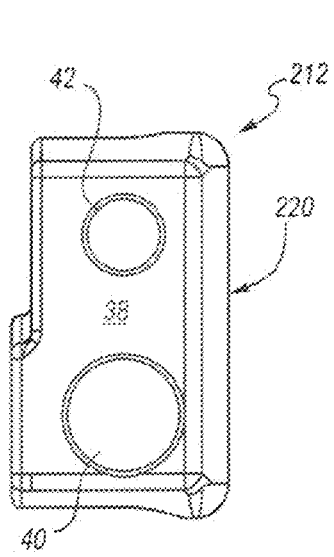
FIG. 23 is a side view of the spine rod connector of FIG. 20.
Figure 22:
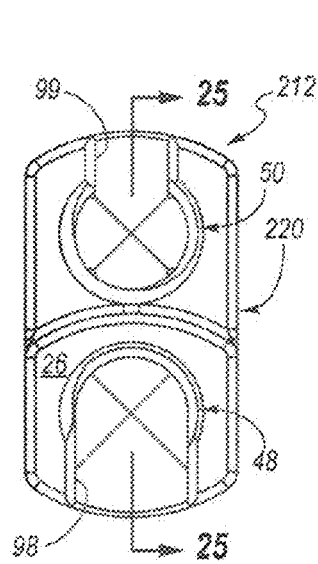
FIG. 22 is a top view of the spine rod connector of FIG. 20.
Figure 25:
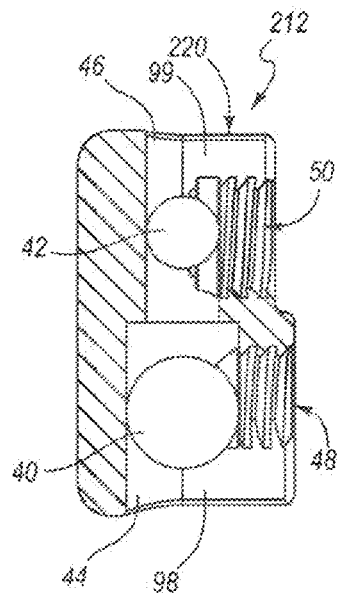
FIG. 25 is a cross-sectional view of the spine rod connector of FIG. 22.
Figure 24:
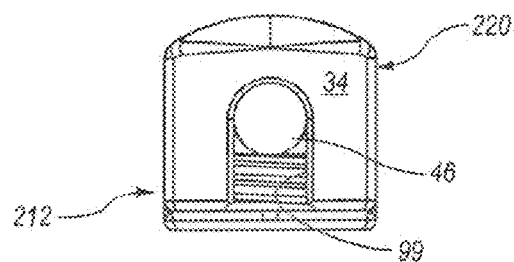
FIG. 24 is an end view of the spine rod connector of FIG. 20.
Figure 26:
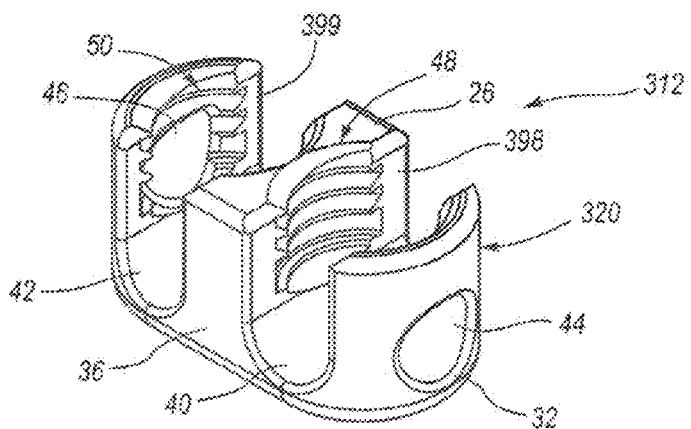
FIG. 26 is a perspective view of another spine rod connector according to the present disclosure.
Figures 27, 28, 30:
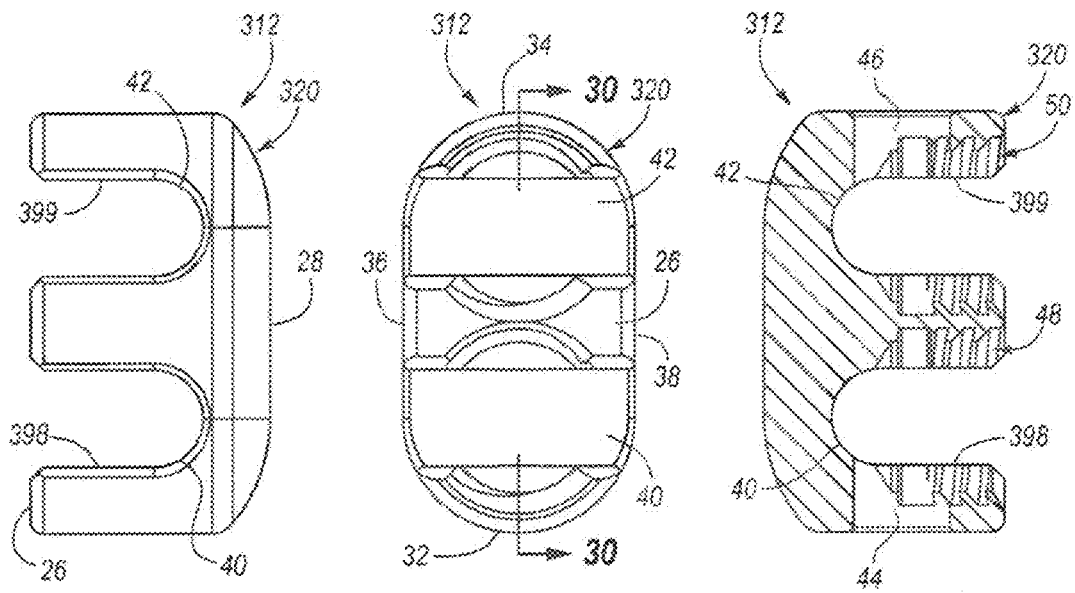
FIG. 27 is a top view of the spine rod connector of FIG. 26.
FIG. 28 is a side view of the spine rod connector of FIG. 26.
FIG. 30 is a cross-sectional view of the spine rod connector of FIG. 27.
Figure 29:
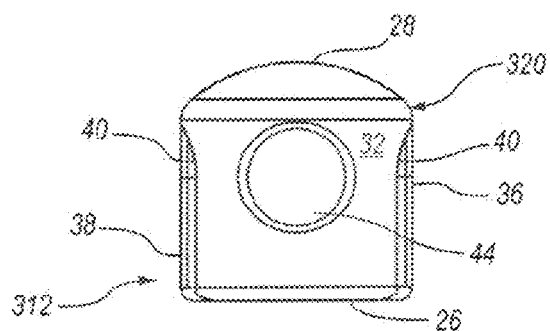
FIG. 29 is an end view of the spine rod connector of FIG. 26.
Figure 31:
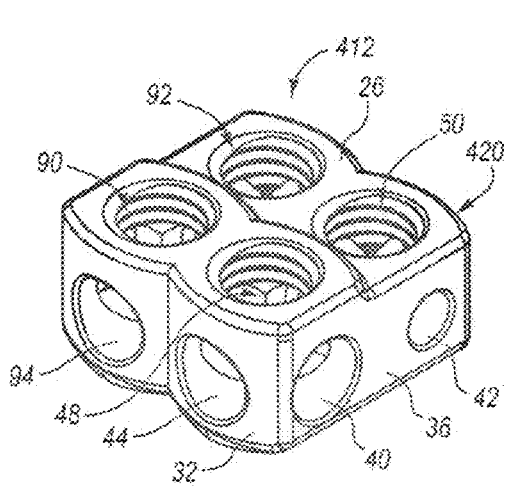
FIG. 31 is a perspective view of another spine rod connector according to the present disclosure.
Figure 32:
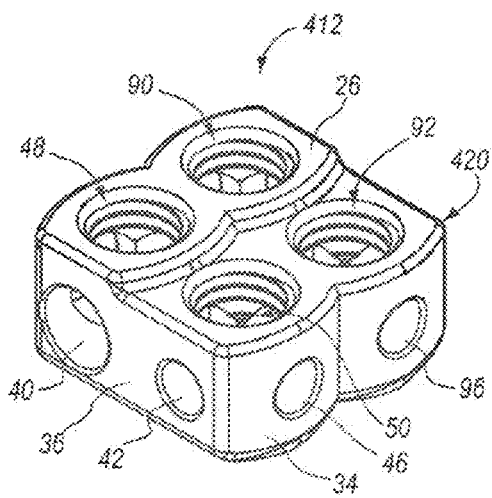
FIG. 32 is another perspective view of the spine rod connector of FIG. 31.
Figure 34:
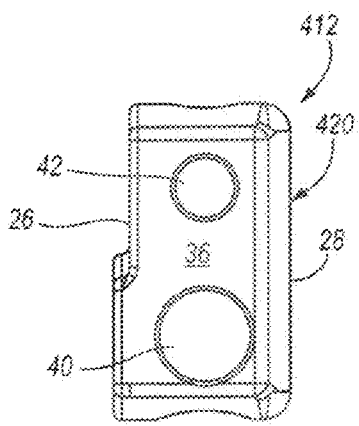
FIG. 34 is a side view of the spine rod connector of FIG. 31.
Figure 33:
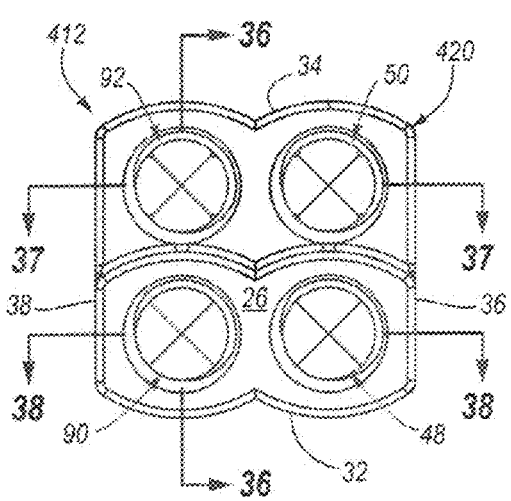
FIG. 33 is a top view of the spine rod connector of FIG. 31.
Figure 35:
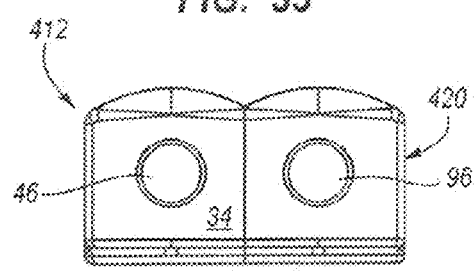
FIG. 35 is an end view of the spine rod connector of FIG. 31.
Figure 36:
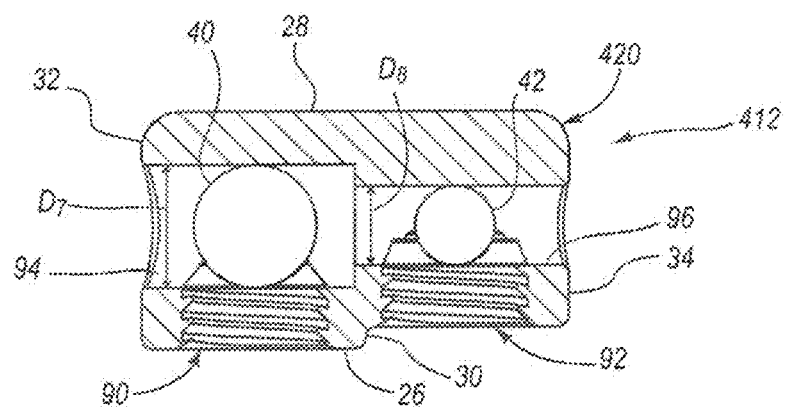
FIG. 36 is a cross-sectional view of the spine rod connector of FIG. 33 taken along cross-sectional indicator 36-36.
Figure 37:
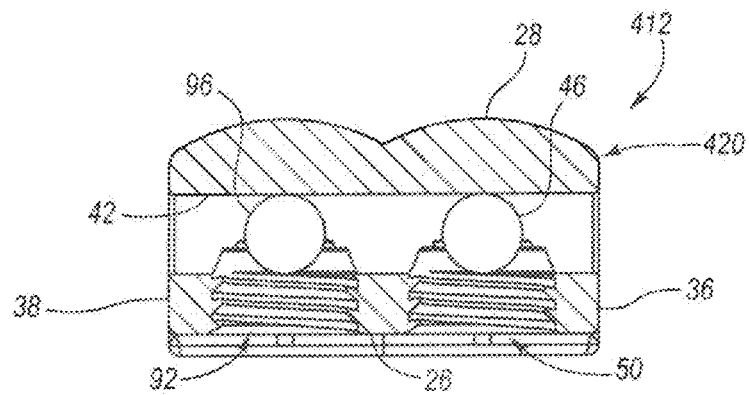
FIG. 37 is a cross-sectional view of the spine rod connector of FIG. 33 taken along cross-sectional indicator 37-37.
Figure 38:
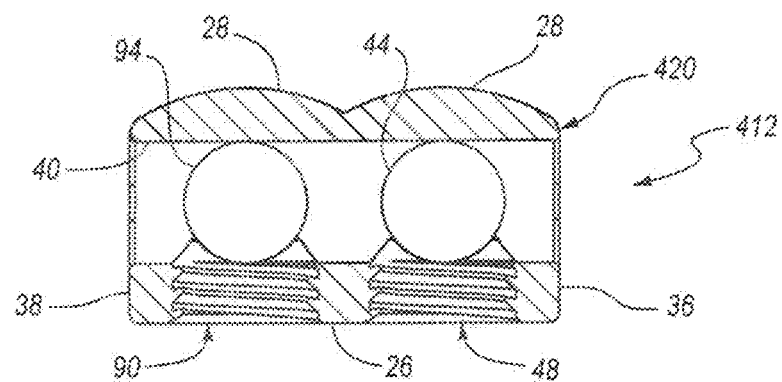
FIG. 38 is a cross-sectional view of the spine rod connector of FIG. 33 taken along cross-sectional indicator 38-38.

Each of the apertures 40, 42 and 44, 46 are arranged in the same plane such that a central, longitudinal axis of each of the apertures 40, 42, 44, 46 is coplanar (see plane $P_1$ in FIGS. 10 and 14). When the spine rods 14, 16 are inserted into the apertures 40, 42, 44, 46 in the various arrangements shown in FIGS. 3, 6 and 9, the spine rods 14, 16 are also arranged coplanar.

The first side rod aperture 40 intersects with the front end aperture 44. The first set screw aperture 48 is arranged perpendicular to and intersects with the apertures 40, 44. Similarly, second side rod aperture 42 intersects with the rear end aperture 46. The second set screw aperture 50 is arranged perpendicular to and intersects the apertures 42, 46. The first and second set screws 22, 24, which are operable in the first and second set screw apertures 48, 50, respectively, may engage spine rods positioned in any of the apertures 40, 42, 44, 46.

In other arrangements, the first side rod aperture 40 and front end aperture 44 are arranged in different planes so that the longitudinal axis of the apertures 40, 44 do not intersect. In such an arrangement, the first set screw aperture 48 may still be arranged to intersect both of the apertures 40, 44. The set screw 22 may require additional length to the length illustrated in the figures to function in such an arrangement in which the apertures 40, 44 are not arranged in the same plane. Similar aperture arrangements are possible for apertures 42, 46, 50.

The front and rear end apertures 44, 46 are arranged both coplanar and axially aligned with each other. The resultant arrangement of spine rods positioned in the apertures 44, 46 as shown in FIGS. 4-6 provides coaxial arrangement of the rods 14, 16. Other arrangements and orientations of the front and rear end apertures 44, 46 are possible. For example, the front and rear end apertures 44, 46 may be arranged coplanar but not coaxial by being arranged at slight converging or diverging angles relative to each other. Alternatively, the front and rear end apertures 44, 46 can be non-coplanar and non-coaxially aligned so as to be arranged at converging or diverging angles in multiple planes.

Figure 39:
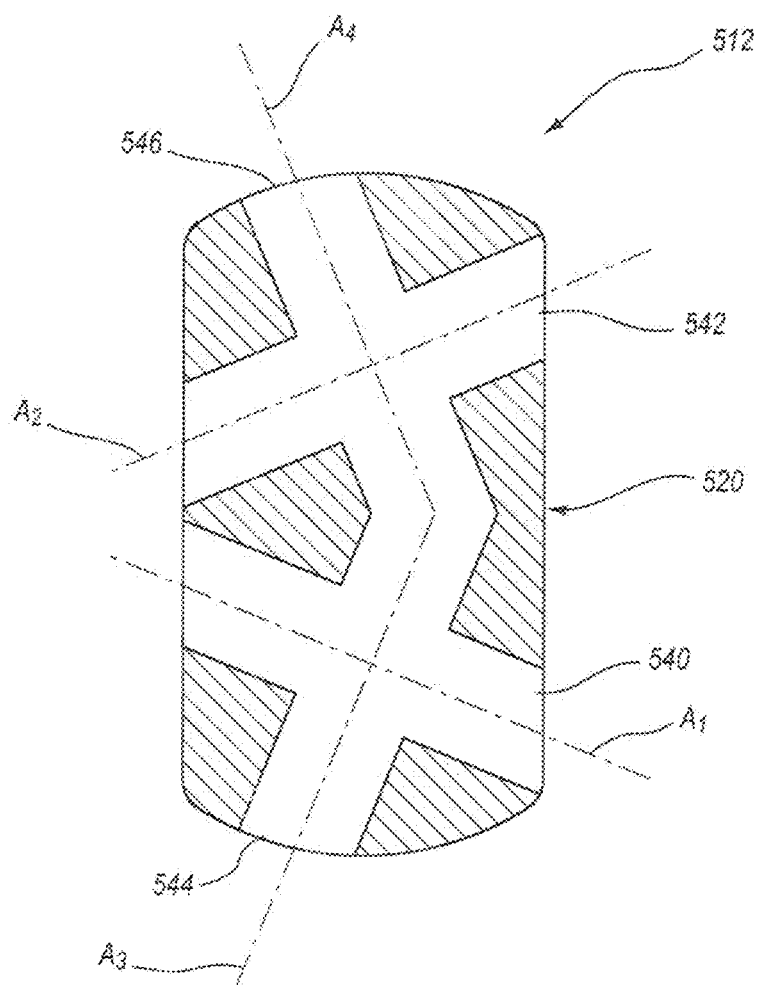
FIG. 39 is a cross-sectional view of another spine rod connector according to the present disclosure.

FIG. 39 is a cross-sectional view illustrating an alternative spine rod connector 512 that includes a base portion 520 and a plurality of apertures 540, 542, 544, 546. The cross-section shown in FIG. 39 can be taken through a plane of the spine rod connection 512 that intersects all of the apertures 540, 542, 544, 546, such as the plane $P_1$ shown in FIG. 10. The apertures 540, 542 have axes $A_1$, $A_2$ that are arranged at convergent/divergent angles relative to each other (i.e., non-parallel angle). The apertures 544, 546 have axes $A_3$, $A_4$ that are also arranged at convergent/divergent angles relative to each other. In at least one example, the apertures 540, 542, 544, 546 are arranged coplanar. In other examples, at least one of the apertures 540, 542, 544, 546 is non-coplanar with the other apertures 540, 542, 544, 546. In yet further examples, at least one pair of apertures 540, 542 or 544, 546 is arranged parallel and the other pair of apertures 540, 542, 544, 546 is arranged at convergent/divergent angles. Other combinations of parallel, perpendicular, and convergent/divergent angled orientations for the apertures 540, 542, 544, 546 are possible.

The step feature 30 may be included on the top surface 26 to make constant a distance from the top surface 26 to the apertures 40, 44 and 42, 46, respectively. With this structure, the sets screws 22, 24 may have the same length and the same number of threads for operation in the first and second set screw apertures 48, 50. Further, there is the same amount of material of the connector member 12 included between the top surface 26 and each of the apertures 40, 44, and 42, 46.

The first and second set screws 22, 24 each include a rod contact end 54, an instrument recess 56 arranged on an opposite side from the rod contact end 54, and a plurality of external threads 58. The rod contact end 54 may have various configurations or structures that permit close mating with the particular rod positioned in the apertures 40, 42, 46, 48. FIGS. 3, 6 and 8 illustrate various configurations for the rod contact end 54. In at least one arrangement, the rod contact end 54 includes a generally planer surface for contact with the spine rods 14, 16. FIGS. 3, 6 and 9 show a rod contact end 54 having a contoured surfaces.

The instrument recess 56 may be structured to receive a portion of an instrument that is used to move the set screws 22, 24 relative to the base portion 20. In other arrangements, the set screws 22, 24 may include recessed portions around an outer or peripheral surface for engagement by an instrument.

The set screws 22, 24 may be replaced with other devices that are operable to secure the spine rods 14, 16 to the base portion 20. For example, rivets, bolts, or other fasteners may be used in place of or in combination with the set screws 22, 24 to provide permanent or releasable contact with the spine rods 14, 16.

Referring now to FIGS. 15-19, another example spine rod connector 112 is shown and described. The spine rod connector 112 includes a base portion 120 that includes top and bottom surfaces 26, 28, front and rear surfaces 32, 34, and first and second side surfaces 36, 38. First and second side rod apertures 40, 42 extend between the first and second side surfaces 36, 38. The first and second side rod apertures have first and second diameters D1, D2, respectively. The front and rear and apertures 44, 46 extend from the front surface 32 to the rear surface 34. The front and rear end apertures 44, 46 have a diameter D3. First and second set screw apertures 48, 50 are defined in the top surface 26 and have a diameter D5. The set screw aperture 48, 50 have a plurality of internal threads 52 sized for threaded engagement with a pair of set screws (not shown), such as set screws 22, 24 described above to reference to FIGS. 1-14.

The first and second side rod apertures 40, 42 have diameters D1, D2, respectively, that are substantially the same. In other arrangements, the diameters D1, D2 may be different. The diameter D3 of the front and rear end apertures 44, 46 is shown as a constant diameter but could have different diameters for each of the apertures 44, 46.

The base portion 20 can have a generally oval outer profile as shown in FIG. 16. Some surfaces of the base portion 20 may have a planer construction (e.g., the planar structure of top surface 26) or a contoured construction (e.g., the contoured construction of bottom surface 28) shown in FIG. 18.

The spine rod connector 112 may be useful in coupling together a plurality of rods in various relative orientations, for example, in parallel, radially spaced apart orientations (i.e., side-by-side), in coaxial orientations (i.e., end-to-end), angled orientations, or perpendicular orientations. In at least some arrangements, the spine rod connector 112 is adapted for use with spine rods having the same diameter, while in other arrangements the spine rod connector 112 can be used with rods of different diameters.

Referring now to FIGS. 20-25, another example spine rod connector 212 is shown and described. The spine rod connector 212 includes a base portion 220 similar in construction with the base portion 20 shown and described above with reference to FIGS. 1-14. The base portion 220 further, includes front and rear aperture slots 98, 99. The front aperture slot 98 provides an open pathway or slot extending from the top surface 26 and the first set screw aperture 48 to the front end aperture 44. The rear aperture slot 99 extends from the top surface and the second set screw aperture 50 to the rear end aperture 46. The aperture slots 98, 99 may promote easier insertion of the spine rods 14, 16 into the apertures 44, 46, respectively. In some arrangements, the first and second set screws 22, 24 are removed from the set screw apertures 48, 50 while the spine rods 14, 16 are inserted into the apertures 44, 46, respectively. The set screws 22, 24 may then be inserted into the set screw apertures 48, 50 in a step that follows insertion of the spine rods 14, 16 into the base portion 20.

FIGS. 26-30 illustrate another example spine rod connector 312 that is a variation of the spine rod connectors 112, 212 described above. The spine rod connector 312 includes a base portion 320. The base portion 320 includes a pair of side aperture slots 398, 399. The side apertures slots 398, 399 extend from the top surface 26 to the first and second side rod apertures 40, 42. The side apertures slot 398, 399 also extend from the first side surface 36 to the second side surface 38 and extend through the first and second set screw apertures 48, 50. In other arrangements, the side apertures slots 398, 399 extend only from the first side surface 36 to one of the set screw apertures 48, 50, or extend only from the second side surface 38 to one of the set screw apertures 48, 50.

The base portion 320 may further include front and rear end apertures 44, 46. In other arrangements, at least one of the front and rear end apertures 44, 46 are not included. In still other arrangements, the apertures 40, 42, 44, 46 may have different sizes and shapes from each other to accommodate different spine rod sizes and cross-sectional shapes. For example, at least one of the apertures 40, 42, 44, 46 can have an elliptical, hexagonal, rectangular, or other non-circular cross-sectional shape as shown in broken lines around apertures 42 and 46 in FIGS. 10 and 13.

Referring now to FIGS. 31-38, a further spine rod connector 412 is shown and described. The spine rod connector 412 includes a base portion 420 having more than two pairs of rod apertures. The base portion 420 is essentially a combination of two base portions 20 coupled in a side-by-side arrangement. The base portion 420 includes the first and second side rod apertures 40, 42, first front and rear end apertures 44, 46, and first and second set screw apertures 48, 50. The first side rod aperture 40 and first front end aperture 44 are arranged as a pair of rod apertures that intersect, and the first set screw aperture 48 is open to the intersection of the apertures 40, 44. Similarly, the second side rod aperture 42 and first rear end aperture 46 are arranged as a pair of rod apertures that is intersected, and the second set screw aperture 50 is open to the intersection of the apertures 42, 46.

The base portion 420 may further include a second front end aperture 94 and a second rear end aperture 96 that intersect with the first and second side rod apertures 40, 42, respectively. Additional third and fourth set screw apertures 90, 92 are open to the intersection of with the second front and rear end apertures 94, 96 with the first ands second side rod apertures 40, 42, respectively. The second front and rear end apertures 94, 96 have seventh and eighth diameters D7, D8, respectively.

The arrangement of apertures shown in FIGS. 31-38 is merely exemplary of the numerous combinations of apertures and set screws that are possible. In at least one example, the apertures 40, 44, 94 have the same diameter, and the apertures 42, 46, 96 have the same diameter. In other arrangements, any one of the aperture 40, 42, 44, 46, 94, 96 may have a different diameter from any of the other apertures 40, 42, 44, 46, 94, 96. Furthermore, any of the configurations described above with reference to FIGS. 1-30 are possible with the spine rod connector 412.

Other spine rod connector possibilities include, for example, two of the spine rod connectors 12, 112, 212, 312 arranged with the bottom surfaces 28 facing each other rather than the side surfaces facing each other as shown in FIGS. 31-38. In yet other arrangements, more than two of the spine rod connectors 12, 112, 212, 312 may be coupled together in various configurations to meet the spine rod orientations needed for treating a particular patient.

While the invention has been particularly shown and described with reference to embodiments thereof, it will be understood by those skilled in the art that various other changes in the form and details may be made without departing from the spirit and scope of the invention.

We claim:

1. A spine rod connector, comprising:
a base portion, including:
opposing top and bottom surfaces;
opposing front and rear surfaces;
opposing first and second side surfaces;
at least a first side rod aperture extending between the first and second side surfaces, the first side rod aperture having a first minimum cross-sectional dimension;
at least a second side rod aperture extending between the first and second side surfaces, the second side rod aperture having a second minimum cross-sectional dimension different than the first minimum cross-sectional dimension;
at least one front rod aperture defined in the front surface and having a third minimum cross-sectional dimension substantially equal to both the first minimum cross-sectional dimension and a first maximum diameter of a first rod, the at least one front rod aperture intersecting the first side rod aperture;
at least one rear rod aperture defined in the rear surface and having a fourth minimum cross-sectional dimension substantially equal to both the second minimum cross-sectional dimension and a second maximum diameter of a second rod, the at least one rear rod aperture intersecting the second side rod aperture;
wherein the first and second side rod apertures and the front and rear rod apertures are cylindrical shaped having a circular cross-section;
at least first and second set screw apertures defined in the top surface, the first set screw aperture intersecting the front rod aperture and the first side rod aperture only, and the second set screw aperture intersecting the rear rod aperture and the second side rod aperture only;
a plurality of set screws, a separate set screw operable in each of the first and second set screw apertures.

2. The spine rod connector of claim 1, wherein the front and rear rod apertures are coaxial.

3. The spine rod connector of claim 1, wherein the first and second set screw apertures are arranged perpendicular to the first and second side rod apertures and the front and rear rod apertures.

4. The spine rod connector of claim 1, wherein the front and rear rod apertures include axes that are arranged coplanar and non-coaxial.

5. The spine rod connector of claim 1, wherein the first and second side rod apertures are arranged coplanar with the front and rear rod apertures.

6. The spine rod connector of claim 1, wherein the top surface includes an offset height feature located between the first and second set screw apertures.

7. The spine rod connector of claim 6, wherein the offset height feature is a step feature.

8. The spine rod connector of claim 1, further comprising a second front rod aperture that intersects with the first side rod aperture, a second rear rod aperture that intersects with the second side rod aperture, a third set screw aperture intersecting the second front rod aperture and the first side rod aperture, and a fourth set screw aperture intersecting the second rear rod aperture and the second side rod aperture.

9. The spine rod connector of claim 1, wherein the first and second side rod apertures have axes that are parallel.

10. A spine rod assembly, comprising:
a spine rod connector, comprising:
a base portion including a first pair of intersecting bores wherein a first bore of the first pair of intersecting bores has a first minimum cross-sectional dimension and a second bore of the first pair of intersecting bores has a second minimum cross-sectional dimension equal to the first minimum cross-sectional dimension, and a second pair of intersecting bores wherein a first bore of the second pair of intersecting bores has a third minimum cross-sectional dimension and a second bore of the second pair of intersecting bores has a fourth minimum cross-sectional dimension equal to the third minimum cross-sectional dimension, the third and fourth minimum cross-sectional dimension different than the first and second minimum cross-sectional wherein the first and second bores of the first and second pairs of intersecting bores are cylindrical shaped having a circular cross-section dimension, the base portion further including a first set screw aperture that intersects the first pair of intersecting bores and a second set screw aperture that intersects the second pair of intersecting bores; and
a plurality of set screws, a separate set screw operable at the intersection of each pair of bores;
a first rod member inserted in one of the bores of the first pair of intersecting bores and arranged for contact by one of the set screws to secure the first rod member to the spine rod connector; and
a second rod member inserted in one of the bores of the second pair of intersecting bores and arranged for contact by one of the set screws to secure the second rod member to the spine rod connector.

11. The spine rod assembly of claim 10, wherein the first bore of the first pair of bores is arranged in parallel with the first bore of the second pair of bores.

12. The spine rod assembly of claim 11, wherein the second bore of the first pair of bores is arranged in parallel with the second bore of the second pair of bores.

13. The spine rod assembly of claim 10, wherein the first bore of the first pair of bores is arranged at a converging angle or a diverging angle relative to a first bore of the second pair of bores.

14. The spine rod assembly of claim 10, wherein the first bore of the first pair of bores is arranged coaxial with the first bore of the second pair of bores.

15. The spine rod assembly of claim 10, wherein the first and second pairs of bores are arranged coplanar.

16. The spine rod assembly of claim 10, wherein the base portion further includes first and second additional bores, and a separate set screw operable at an intersection of the first additional bore with one bore of the first pair of bores and a separate set screw operable at an intersection of the second additional bore with one bore of the second pair of bores.

17. The spine rod assembly of claim 16, wherein the first and second additional bores are arranged coaxial with each other.

18. The spine rod assembly of claim 17, wherein the first and second additional bores have different diameters.

19. A method of connecting first and second spine rods using a spine rod connector, the method including:
providing a spine rod connector comprising a first pair of intersecting bores and a second pair of intersecting bores, where each pair of intersecting bores are generally perpendicular, and wherein a first bore of the first pair of intersecting bores has a first bore diameter and a second bore of the first pair of intersecting bores has a second bore diameter equal to the first bore diameter and a first bore of the second pair of intersecting bores has a third bore diameter and a second bore of the second pair of intersecting bores has a fourth bore diameter equal to the third bore diameter; wherein the first and second bore diameters are different than the third and fourth bore diameters, wherein the first and second bores of the first and second pairs of intersecting bores are cylindrical shaped having a circular cross-section, the spine rod connector further comprising a first set screw aperture intersecting the first pair of intersecting bores and a second set screw aperture intersecting the second pair of intersecting bores selecting which bore of the first pair of intersecting bores to receive the first spine rod and which bore of the second pair of intersecting bores to receive the second spine rod;
inserting the first spine rod in the selected bore of the first pair of intersecting bores, the first spine rod having a size corresponding to the first maximum bore diameter;
securing the first spine rod to the spine rod connector;
inserting the second spine rod in the selected bore of the second pair of intersecting bores, the second spine rod having a size corresponding to the third bore diameter;
securing the second spine rod to the spine rod connector.

20. The method of claim 19, wherein inserting the second spine rod includes arranging the second spine rod generally parallel with the first spine rod.

21. The method of claim 19, wherein inserting the second spine rod includes arranging the second spine rod generally perpendicular with the first spine rod.

22. The method of claim 19, wherein at least one bore of the first pair of bores is arranged coaxial with at least one bore of the second pair of bores, and wherein inserting the second spine rod includes arranging the second spine rod generally coaxial with the first spine rod.

* * * * *